United States Patent
Blomström

(10) Patent No.: US 11,399,991 B2
(45) Date of Patent: Aug. 2, 2022

(54) PACKAGE OF ABSORBENT UNITS AND A METHOD FOR MANUFACTURING SUCH A PACKAGE

(71) Applicant: Essity Hygiene and Health Aktiebolag, Gothenburg (SE)

(72) Inventor: Philip Blomström, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 17/418,297

(22) PCT Filed: Feb. 15, 2019

(86) PCT No.: PCT/SE2019/050138
§ 371 (c)(1),
(2) Date: Jun. 25, 2021

(87) PCT Pub. No.: WO2020/167174
PCT Pub. Date: Aug. 20, 2020

(65) Prior Publication Data
US 2022/0040012 A1 Feb. 10, 2022

(51) Int. Cl.
*A61F 13/15* (2006.01)
*A61F 13/551* (2006.01)
(52) U.S. Cl.
CPC .. *A61F 13/55115* (2013.01); *A61F 13/15577* (2013.01); *A61F 13/55135* (2013.01)
(58) Field of Classification Search
CPC .......... A61F 13/55115; A61F 13/15577; A61F 13/55135
See application file for complete search history.

(56) References Cited

U.S. PATENT DOCUMENTS 8,220,632 B2   7/2012  Oi et al.
8,939,955 B2   1/2015  Oates
(Continued)

FOREIGN PATENT DOCUMENTS

AU   2010235860 A1   5/2011
CN     1592703 A     3/2005
(Continued)

OTHER PUBLICATIONS

Brainard, D.H., "Color Appearance and Color Difference Specification", The Science of Color, 2003, pp. 191-216, ISBN 0-444-512-519, Elsevier, Ltd. (26 pages).
(Continued)

*Primary Examiner* — Jacqueline F Stephens
(74) *Attorney, Agent, or Firm* — Buchanan Ingersoll & Rooney PC

(57) ABSTRACT

The present disclosure relates to a package (1) of absorbent units (5; 11), said package (1) includes an outer enclosure (2) enclosing the absorbent units (5; 11) and being at least partially non-opaque, wherein the outer enclosure (2) has a thickness (t) which is not more than approximately 70 μm, wherein the outer enclosure (2) supports a first graphical item (3) and at least one of the absorbent units (5; 11) supports a second graphical item (9; 9'). Furthermore, the absorbent unit (5; 11) supporting said second graphical item (9; 9') is configured so that the second graphical item (9; 9') is positioned in a manner so that it is generally not visible for a viewer from outside the outer enclosure (2). The invention also relates to a method for manufacturing a package (1) of the above-mentioned type.

11 Claims, 3 Drawing Sheets

(56) References Cited

U.S. PATENT DOCUMENTS

| | | |
|---|---|---|
| 9,278,035 B2 | 3/2016 | Hashino et al. |
| 9,308,139 B2 | 4/2016 | Hashino et al. |
| 2007/0212502 A1 | 9/2007 | Hansborough |
| 2007/0267322 A1 | 11/2007 | Kishida et al. |
| 2012/0310201 A1 | 12/2012 | Oates |
| 2013/0098795 A1 | 4/2013 | Biber |
| 2013/0225730 A1 | 8/2013 | Allen et al. |
| 2022/0062071 A1 | 3/2022 | Blomström |

FOREIGN PATENT DOCUMENTS

| | | |
|---|---|---|
| CN | 101442968 A | 5/2009 |
| CN | 101442969 A | 5/2009 |
| CN | 103140197 A | 6/2013 |
| CN | 103429204 A | 12/2013 |
| CN | 103889854 A | 6/2014 |
| CN | 206142077 U | 5/2017 |
| EP | 2623077 A1 | 8/2013 |
| EP | 2689757 A1 | 1/2014 |
| JP | 2000238875 A | 9/2000 |
| RU | 2505575 C2 | 1/2014 |
| RU | 2546482 C2 | 4/2015 |
| WO | 2007132434 A1 | 11/2007 |
| WO | 2012157620 A1 | 11/2012 |
| WO | 2020167175 A1 | 8/2020 |

OTHER PUBLICATIONS

International Preliminary Report on Patentability (PCT/IPEA/409) issued in corresponding International Patent Application No. PCT/SE2019/050138 dated Mar. 25, 2021. (10 pages).

International Search Report (PCT/ISA/210) and Written Opinion (PCT/ISA/237) dated Oct. 29, 2019, by the Swedish Patent Office as the International Searching Authority for International Application No. PCT/SE2019/050138. (12 pages).

International Search Report (PCT/ISA/210) and Written Opinion (PCT/ISA/237) dated Oct. 29, 2019, by the Swedish Patent Office as the International Searching Authority for International Application No. PCT/SE2019/050139. (15 pages).

Mokrzycki, W.S., et al., "Colour Difference ΔE—A Survey", Machine Graphics & Vision, 2011, pp. 383-411, vol. 20, No. 4, The Library of the The Swedish Patent and Registration Office (SLI04X00560E). (29 pages).

Written Opinion of the International Preliminary Examining Authority (PCT/IPEA/408) issued in corresponding International Patent Application No. PCT/SE2019/050138 dated Feb. 16, 2021. (5 pages).

Notification of the First Office Action dated Oct. 27, 2021, by the Chinese Patent Office in corresponding Chinese Patent Application No. 201980087896.2, and an English Translation of the Office Action. (17 pages).

Office Action (Examination Report No. 1) dated Mar. 24, 2022, by the Australian Patent Office in corresponding Australian Patent Application No. 2019429161. (2 pages).

Office Action (Notification of the Second Office Action) dated Apr. 11, 2022, by the Chinese Patent Office in corresponding Chinese Patent Application No. 201980087896.2, and an English Translation of the Office Action. (22 pages).

Office Action dated Mar. 31, 2022, by the Russian Patent Office in corresponding Russian Patent Application No. 2021126930, and an English Translation of the Office Action. (11 pages).

Opposition issued in corresponding Colombian Patent Application No. NC2021/0009298, the Opposition was filed on Oct. 26, 2021 and admitted on Nov. 22, 2021 (14 pages).

Office Action (Examination Report No. 1) dated Nov. 23, 2021, by the Australian Patent Office in corresponding Australian Patent Application No. 2019429635. (4 pages).

Office Action (Notification of the First Office Action) dated Dec. 16, 2021, by the Chinese Patent Office in corresponding Chinese Patent Application No. 201980087889.2, and an English Translation of the Office Action. (22 pages).

Third Party Observation issued in corresponding Mexican Patent Application No. MX/E/2021/091448, dated Dec. 14, 2021 (15 pages).

Office Action dated Dec. 21, 2021, by the Russian Patent Office in corresponding Russian Application No. 2021122389, and an English Translation of the Office Action. (15 pages).

PACKAGE OF ABSORBENT UNITS AND A METHOD FOR MANUFACTURING SUCH A PACKAGE

TECHNICAL FIELD

The disclosure relates to a package of absorbent units. The disclosure also relates to a method for manufacturing a package of absorbent units.

BACKGROUND

Absorbent articles, for example in the form of sanitary napkins, panty liners, diapers and incontinence pads are well known. The general purpose of such absorbent articles is to absorb, distribute and store various types of body exudates while providing a high level of comfort and sense of dryness to the wearer during use. Also, such absorbent articles are arranged to prevent the wearer from getting the clothes soiled by body exudates.

For marketing and sale of absorbent articles, it is previously known to provide packages of such articles. Typically, a number of absorbent articles are formed as a stack which is contained within an outer enclosure, for example in the form of a flexible wrapping, so as to form a package. As a first alternative, each absorbent article can be enclosed in an individual wrapping material before such a stack is formed and enclosed within the outer enclosure. As a further alternative, the stack can be formed by a number of absorbent articles without any individual wrapping of each article.

According to prior art, the outer enclosure is normally produced from a relatively thin layer of a flexible material, such as polyethylene, which is formed as a bag-like outer enclosure. This means that a number of absorbent articles can be packed into the enclosure so as to form the final package of absorbent products.

During a packaging process, the outer enclosure is normally provided with various types of graphical items such as for example one or more logotypes and areas with printed text which indicate, for example, the name and type of product which is contained within the package. Furthermore, the basic material which is used for the outer enclosure is normally coloured or transparent when it enters the above-mentioned packaging process.

In order for the final package to give the customer a visual and aesthetic appearance which indicates that the absorbent product in question is a premium product which is of high quality, it has been proposed that the outer enclosure should be configured as a dark or opaque material so that any occurring graphical markings, logotypes or visual features on the actual absorbent products (or their individual wrapping material, if this is used) are not visible from the outside, i.e. so that they are not visible through the outer enclosure material. In other words, a "see-through" type of outer enclosure material is unwanted, in particular for the described premium products.

However, the design trends relating to today's absorbent consumer products may require that the outer enclosure is designed and manufactured in the form of very light or pale colours, i.e. colours having a relatively small amount of colouring substance. Also, the need for a cost-efficient manufacturing process may require that the outer enclosure is made from a very thin layer of material, suitably having a thickness which is not more than approximately 70 µm. This will result in an enclosure material which is at least partly non-opaque. Due to this, it has been noted that it is difficult to form the outer enclosure and the absorbent articles in a manner to avoid that graphical markings, logotypes, text areas or visual patterns on the absorbent products are actually visible from the outside, i.e. through the material of the outer enclosure. This is a disadvantage within the relevant field of technology.

In this regard, it should be noted that the aesthetic qualities of the outer design of a package of absorbent articles is increasingly important since it will affect the way in which the customers perceive the articles and their properties.

A previously known packaged absorbent product is described in the patent document US 2007/0267322. This document shows a package comprising a plurality of absorbent articles and at least one window. The package is based on a desire to show a graphic on at least one of the absorbent articles.

Even though the article disclosed in US 2007/0267322 discloses a package for a number of absorbent articles which is intended to give a customer a particular visual impression, there is a need for further improvements within this field of technology. In particular, there is an increasing requirement to provide an improved package which can be configured so as to indicate to a customer that the absorbent product in question has particular properties. In this regard, it is particularly important to give a user the impression that the products are of premium quality.

Consequently, there is a need for further improvements within the above-mentioned field of technology.

SUMMARY

In accordance with the disclosure, there is provided a package of absorbent articles having a purpose of solving the above-mentioned problems related to prior art within this field. In particular, the article is configured so as to provide a package which gives a particular visual impact to the customer and in particular in which any graphical items on the absorbent products are generally not visible for a viewer who watches the package from the outside of the outer enclosure of the package.

In accordance with the disclosure, this object is obtained by means of a package of absorbent units, said package comprising an outer enclosure enclosing said absorbent units and being at least partially non-opaque, wherein said outer enclosure has a thickness which is not more than approximately 70 µm, wherein said outer enclosure supports a first graphical item and at least one of said absorbent units supports a second graphical item. Furthermore, said absorbent unit supporting said second graphical item is configured so that said second graphical item is positioned in a manner so that it is generally not visible for a viewer from outside the outer enclosure.

According to the disclosure, an advantage is provided through the fact that it fulfills the object of giving the user of the absorbent article a positive visual impact regarding the properties of the article.

The package may be configured so that said second graphical item is covered by the first graphical item.

The package may be configured so that said outer enclosure is manufactured from a material with an opacity which is not higher than approximately 70%.

The opacity value of the outer enclosure may be chosen depending on the intensity of the second graphical item so that said second graphical item is not visible for a viewer from outside the outer enclosure.

The package may be configured so that each one of said absorbent units is constituted by an inner enclosure which encloses an absorbent product, and wherein said second graphical item is positioned on the outside of said inner enclosure.

The package may be configured so that each one of said absorbent units is constituted by an absorbent product, and wherein said second graphical item is positioned on said absorbent product.

The package may be configured so that said second graphical item is positioned so that it faces the inside of the outer enclosure and wherein said first graphical item covers said second graphical item.

The package may be configured so that the absorbent unit supporting said second graphical item is configured so that second graphical item faces inwards into said outer enclosure.

The package may be configured so that said absorbent unit is arranged in a folded configuration.

The package may be configured so that said first graphical item is arranged on the exterior side of said outer enclosure.

The package may be configured so that said first graphical item and said second graphical item are constituted by printed areas or areas comprising coloured sections, adhesive stickers, logotypes, text boxes or graphical markings.

The package may be configured so that the outer enclosure has a thickness which is less than approximately 70 μm.

The package may be configured so that the outer enclosure has a thickness which is less than approximately 60 μm and most preferably less than 50 μm.

According to the disclosure, there is also provided a method for manufacturing a package of absorbent units, said method comprising: providing an outer enclosure which is at least partially non-opaque and which has a thickness which is not more than approximately 70 μm; arranging said outer enclosure so that it encloses said absorbent units; arranging said outer enclosure so that it supports a first graphical item; and arranging at least one of said absorbent units so that it supports a second graphical item. Furthermore, the method comprises configuring said absorbent unit which supports said second graphical item so that said second graphical item is positioned so that said second graphical item is not visible for a viewer from outside of the outer enclosure.

Further advantages and advantageous features of the disclosure are disclosed in the following description and in the dependent claims.

In the following, the term "absorbent unit" is used to indicate either a unit in the form of an absorbent article including an individual wrapping or a unit in the form of an absorbent article without such individual wrapping. The disclosure is consequently equally applicable to packages comprising either one of these types of absorbent units.

BRIEF DESCRIPTION OF THE FIGURES

The disclosure will be described in greater detail below with reference to the figures shown in the appended drawings.

DETAILED DESCRIPTION

Different aspects of the present disclosure will be described more fully hereinafter with reference to the enclosed drawings. The disclosure can be realized in many different forms and should not be construed as being limited to the embodiments below.

Figure 1:
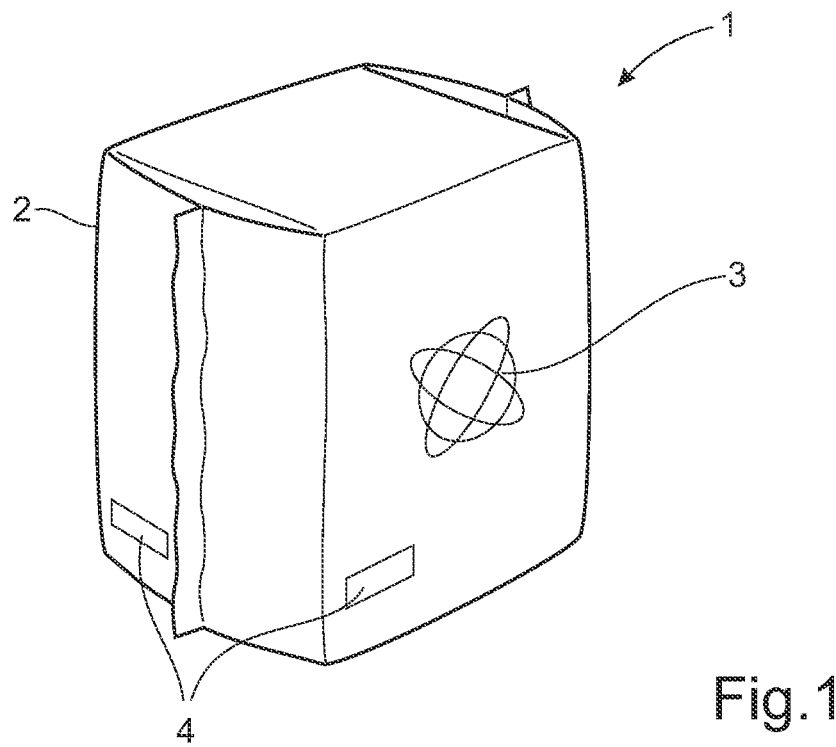
FIG. 1 shows a perspective view of a package of absorbent units according to a first embodiment.

With initial reference to FIG. 1, there is shown a perspective view of a package 1 which is intended to contain a number of absorbent units. The actual absorbent units are not visible in FIG. 1 but will be described in detail below with reference to FIGS. 2-4. It should be noted that the package 1 is suitable for absorbent units such as sanitary napkins, panty liners, diapers and incontinence pads, which can be packaged either with or without an individual wrapping. The package 1 is also suitable for other types of absorbent hygienic articles such as wet wipes.

The package 1 according to FIG. 1 is formed by an outer enclosure 2 which according to the embodiment is manufactured from a thin layer of a polymer material, suitably polyethylene, which is a flexible material which can be formed as a bag-like enclosure to accommodate the absorbent units. According to further embodiments, the outer enclosure 2 can be manufactured from other materials, for example polypropylene or cellulose-based materials, suitably in the form of a polyethylene film or film laminate, a LDPE (low density polyethylene film), a LDPE/LLDPE (linear low density polyethylene) film laminate, a LDPE/MDPE (medium density polyethylene) film laminate, or a LDPE/HDPE (high density polyethylene) film laminate.

In accordance with today's demands, the outer enclosure 2 is formed from a material which has a thickness which is not more than approximately 70 μm. According to an embodiment, the outer enclosure has a thickness t of approximately 40-45 μm.

The outer enclosure 2 is provided with at least one graphical item 3, which according to the embodiment of FIG. 1 is in the form of a logotype which is printed on the outer enclosure 2. The outer enclosure 2 can also be provided with one or more additional graphical items 4. Also, as shown in FIG. 1, the graphical items 3, 4 can be provided on one or more of the side surfaces of the outer enclosure 2. Examples of graphical items which can be used are decorative drawings, photographs and text sections. These graphical items are normally printed on the outer enclosure 2. According to further embodiments, the graphical item can be in the form of one or more adhesive stickers which can be attached to the outer enclosure 2.

Figure 2:
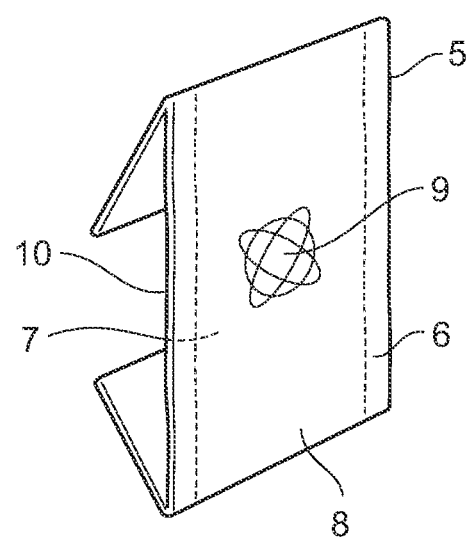
FIG. 2 shows a perspective view of an absorbent unit.
Figure 3:
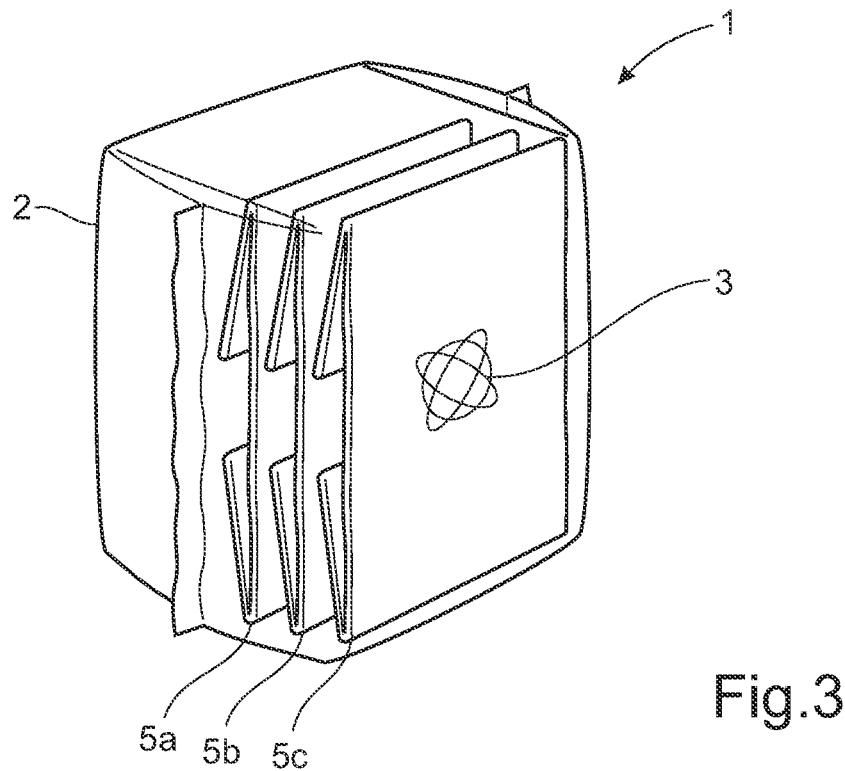
FIG. 3 shows a perspective view of a package showing also a number of absorbent units.

With reference to FIG. 2, there is shown an absorbent unit 5 which is intended to be packaged in the outer enclosure 2 of FIG. 1. The absorbent unit 5 is shown in a folded configuration. Also, during manufacturing of the package 1, a number of such absorbent units 5a, 5b, 5c are formed as a stack and are enclosed by the outer enclosure 2. This is shown in FIG. 3. For reasons of clarity, the outer enclosure 2 is drawn as a transparent component in FIG. 3. In reality, the absorbent units 5a, 5b, 5c are generally not intended to be visible from the outside.

According to an embodiment shown in FIG. 2, the absorbent unit 5 is constituted by an absorbent product in the form of a sanitary napkin which is designed and manufactured in a generally known manner. This means that it comprises a liquid-impermeable backsheet 6, a liquid-permeable topsheet 7 and an absorbent core 8 which is sandwiched between the backsheet 6 and the topsheet 7. The topsheet 7 is arranged at the surface of the absorbent unit 5 i.e. the side facing the wearer during use of the unit 5. The backsheet 6 is arranged at the underside of the absorbent unit 5, i.e. the side facing an undergarment (not shown) of the wearer during use.

As known, the absorbent unit 5 is configured as an absorbent structure for absorbing body exudates from a wearer in order to provide a dry, comfortable and odor-free feeling for the wearer. It should be noted that absorbent units 5 such as the one shown in FIG. 2 are generally known as such and for this reason they are not described in detail here.

According to the embodiment in FIG. 2, the absorbent product 5 comprises a further graphical item 9 in the form of a logotype, which is suitably designed with a similar visual appearance as the graphical item 3 on the surface of the outer enclosure 2. In a manner which corresponds to the outer enclosure 2, the graphical item 9 on the absorbent unit 5 can be in the form of a printed logotype, a drawing, a photograph or a text section, or alternatively an adhesive sticker. It should be noted that, in principle, the graphical item 9 on the absorbent unit 5 can be positioned on the backsheet 6, the topsheet 7 or even along a longitudinal edge 10 of the absorbent unit 5.

In the following, the graphical item 3 on the outer enclosure 2 will be referred to as a "first graphical item" 3 and the graphical item 9 on the absorbent unit 5 will be referred to as a "second graphical item" 9.

Also, the graphical items 3, 9 can be in the form of synchronized printed items, i.e. items which during manufacturing are positioned at a predetermined position on the outer enclosure 2 and the absorbent unit 5, respectively, or can alternatively be in the form of unsynchronized printed items.

According to the embodiment shown in FIG. 2, the absorbent unit 5 is folded before being packaged in the outer enclosure 2. Also, with further reference to FIG. 3, a plurality of such absorbent units 5a, 5b, 5c will be stacked together in their folded condition so as to form the finished package 1. According to various embodiments, the absorbent units can be folded or unfolded, and can also be provided with one or more graphical items on various positions on any surface.

In summary, the disclosure relates to a package 1 of absorbent units 5 which comprises an outer enclosure 2 which is configured to enclose and accommodate the absorbent units 5. In this regard, it should be noted that today's design trends for absorbent products may require that the basic material of the outer enclosure 2 is chosen from materials having relatively light or pale colours, such as white, cream, light yellow, light pink, light blue, light green or other pastel-like colours. This means that the outer enclosure 2 may be based on a material which is at least partly non-opaque. As mentioned above, the outer enclosure 2 is according to an embodiment made of a thin flexible layer of polyethylene or a similar material. Furthermore, as shown in FIGS. 2 and 3, the outer enclosure 2 supports a first graphical item 3 and at least one of said absorbent units 5 (i.e. referred to as 5a, 5b, 5c in FIG. 3) supports a second graphical item 9.

For reasons explained above, it is an object of the disclosure to provide a package 1 which is configured so that the second graphical item 9 is not visible as regarded by a viewer from the outside and through the outer enclosure 2. To this end, the absorbent unit 5 which supports the second graphical item 9 is configured so that the second graphical item 9 is positioned in a manner in relation to said first graphical item 3 so that said second graphical item 9 is not visible through the outer enclosure 2. According to the embodiment shown in FIG. 3, this is accomplished by positioning the absorbent units 5a, 5b, 5c in a manner so that the second graphical item 9 is covered by the first graphical item 3 and for this reason is not visible from the outside of the package 1. In this regard, it should be noted that the second graphical item 9 as shown in FIG. 2 is positioned so that it faces the inside of the outer enclosure 2 whereas the first graphical item 3 is positioned on top of the second graphical item 9 so that it covers the second graphical item 9.

Figure 4:
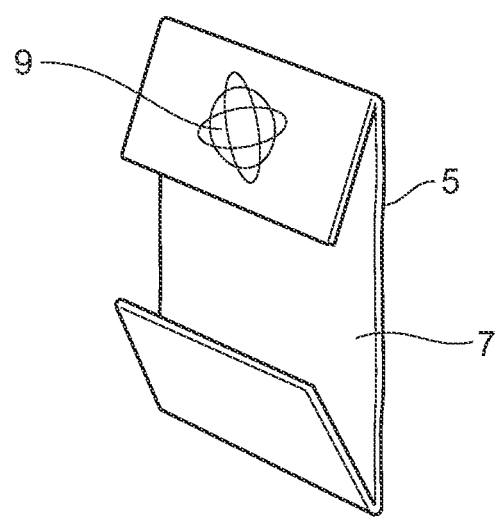
FIG. 4 shows a further perspective view of a further absorbent unit.

According to a further embodiment, which is shown in FIG. 4, the second graphical item 9 is placed on a side of the absorbent unit 5 which does not face the outer enclosure 2, i.e. so that the absorbent unit 5 is configured so that second graphical item 9 faces inwards into the interior of said outer enclosure 2. In this way also, the absorbent unit 5 will be configured so that the second graphical item 9 is positioned in a manner in relation to the first graphical item 3 so that said second graphical item 9 is not visible through the outer enclosure 2.

Furthermore, both the first graphical item 3 and the second graphical item 9 can, according to different embodiments, be constituted by printed logotypes, printed areas or areas comprising coloured sections, adhesive stickers or other graphical markings.

Figure 5:
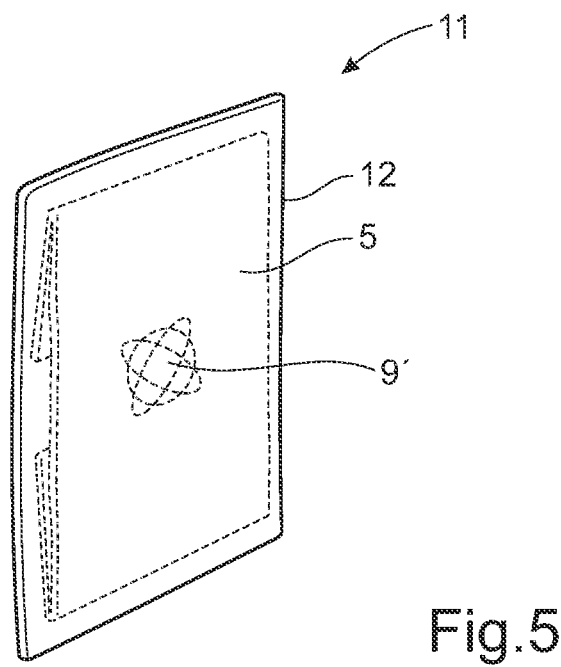
FIG. 5 shows a perspective view of an absorbent unit according to a further embodiment.

With reference to FIG. 5, there is shown a further embodiment involving an absorbent unit 11 which is constituted by an absorbent article 5 (of the same type as shown in FIG. 2) which is enclosed inside an inner enclosure 12. This inner enclosure 12 corresponds to an individual wrapping of the absorbent article 5, i.e. a wrapping sheet which encloses the absorbent article and which suitably is of the same type of material as the outer enclosure 2. Also, a second graphical item 9' is positioned on the outside of the inner enclosure 12. According to this embodiment, there is consequently no graphical item on the absorbent article 5 itself. Consequently, in the embodiment according to FIG. 5, the term "absorbent unit" is used to indicate a unit in the form of an absorbent article including an individual wrapping, which is another embodiment than an absorbent article without such individual wrapping (i.e. as shown in FIGS. 2 and 4). It should be noted that the disclosure is applicable to packages comprising either one of these types of absorbent units.

According to an embodiment, the outer enclosure 2 is manufactured from a material with an opacity which is not higher than a predetermined limit value. Suitably, this opacity limit value is approximately 70%. The opacity of a material corresponds to the degree to which light is not allowed to pass through it. Accordingly, a fully opaque material with 100% opacity is completely impervious to light, whereas a material with 0% opacity is completely transparent.

Figure 6:
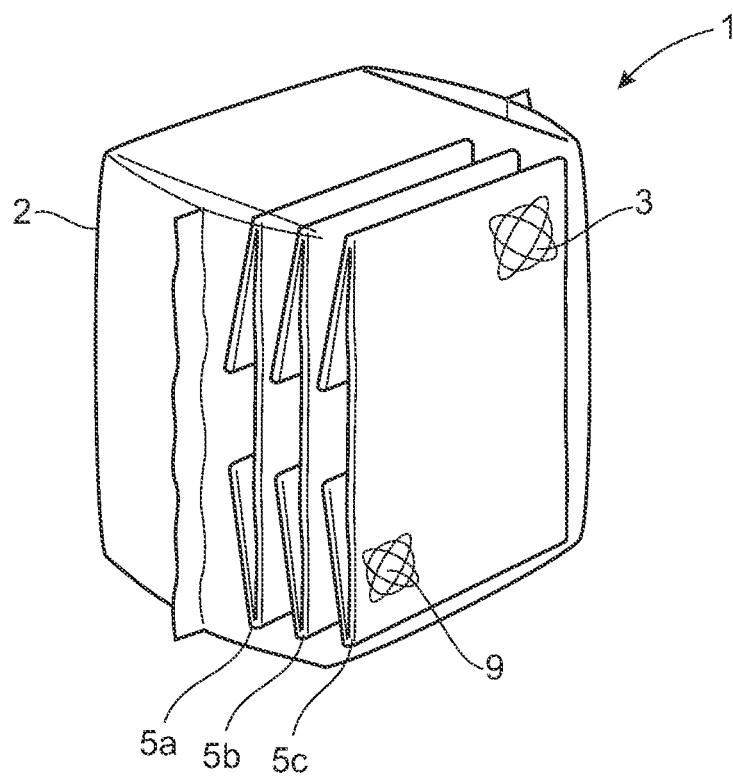
FIG. 6 shows a perspective view of an absorbent unit according to a further embodiment.

FIG. 6 shows an embodiment with an outer enclosure 2 which at least partly has an area with an opacity which is higher than said limit value, which is enough in order to prevent the second graphical item 9 from being visible from the outside. Consequently, the embodiment of FIG. 6 shows that the absorbent unit 5, which supports the second graphical item 9, is configured so that the second graphical item 9 is positioned in a manner so that it will not be visible for a viewer from outside the outer enclosure 2. More precisely, the second graphical item 9 is positioned so that it is aligned with at least the part of the outer enclosure 2 which has an area having an opacity which is higher than said limit value.

According to a further embodiment, the opacity value (0-100%) of the outer enclosure 2 can furthermore be chosen depending on the intensity of the second graphical item 9 so that the second graphical item 9 is not visible.

A process for manufacturing the package of absorbent units 2 as described above comprises a number of steps which will now be described. Initially, a material which is at least partially non-opaque is provided, to be used as an outer enclosure 2. The outer enclosure 2 has a thickness t which is not more than approximately 70 μm, preferably less than 60 μm, more preferably less than 50 μm, and most preferably within the interval 40-μm.

Next, the outer enclosure 2 material is arranged so that it encloses a number of absorbent units 5; 11. Furthermore, the outer enclosure 2 is configured so that it supports a first graphical item 3 of the type which is described above. Furthermore, the absorbent units 5; 11 are arranged so that they support a second graphical item 9; 9'. Also, the absorbent unit 5; 11 which supports the second graphical item 9; 9' is configured so that the second graphical item 9; 9' is positioned so that the second graphical item 9; 9' is not visible for a viewer from outside of the outer enclosure 2.

In order to implement the embodiments of the present disclosure, the following description of measuring methods is provided.

Film Thickness:

The thickness of a film—such as the film being used for the outer enclosure 2—is measured with a foil thickness gauge, model 497 from Erichsen Gmbh (or an equivalent apparatus). Thickness is measured under a pressure of 40 kPa. The pressure is applied from a circular foot with a diameter of about 6 mm.

Opacity:

Opacity is measured with a CM-5 Spectrophotometer from Konica-Minolta (or an equivalent apparatus having diffuse illumination). Configure the spectrophotometer to the XYZ color scale, D65 illuminant and 10° standard observer. Place the sample flat over the measurement aperture and cover the sample with the white ceramic standard plate that comes with the spectrophotometer. Take a first reading. Then cover the sample with a black standard plate and take a second reading. The opacity is then calculated as follows:

$$\text{Opacity (\%)} = (Y \text{ value with the black backing}/Y \text{ value with the white backing}) \times 100$$

Representative measurements are taken all over the outer enclosure, and the mean opacity is reported.

The invention is not limited to the embodiment but can be varied within the scope of the appended claims.

The invention claimed is:

1. A package of absorbent units, said package comprising an outer enclosure enclosing said absorbent units and being at least partially non-opaque, wherein said outer enclosure has a thickness (t) which is less than 50 μm, wherein said outer enclosure supports a first graphical item and at least one of said absorbent units supports a second graphical item, wherein said absorbent unit supporting said second graphical item is configured so that said second graphical item is positioned in a manner so that it is generally not visible for a viewer from outside the outer enclosure and wherein said second graphical item is covered by the first graphical item, and wherein said outer enclosure is manufactured from a material with an opacity which is not higher than approximately 70%.

2. A package according to claim 1, wherein the opacity value of the outer enclosure is chosen depending on the intensity of the second graphical item so that said second graphical item is not visible for a viewer from outside the outer enclosure.

3. A package according to claim 1, wherein each one of said absorbent units is constituted by an inner enclosure which encloses an absorbent product, and wherein said second graphical item is positioned on the outside of said inner enclosure.

4. A package according to claim 1, wherein each one of said absorbent units is constituted by an absorbent product, and wherein said second graphical item is positioned on said absorbent product.

5. A package according to claim 4, wherein the absorbent unit supporting said second graphical item is configured so that second graphical item faces inwards into said outer enclosure.

6. A package according to claim 1, wherein said second graphical item is positioned so that it faces the inside of the outer enclosure and wherein said first graphical item covers said second graphical item.

7. A package according to claim 1, wherein said absorbent unit is arranged in a folded configuration.

8. A package according to claim 1, wherein said first graphical item is arranged on the exterior side of said outer enclosure.

9. A package according to claim 1, wherein said first graphical item and said second graphical item are constituted by printed areas or areas comprising coloured sections, adhesive stickers, logotypes, text boxes or graphical markings.

10. A package according to claim 1, wherein the thickness (t) is less than approximately 60 μm.

11. A method for manufacturing a package of absorbent units, said method comprising:
   a. providing an outer enclosure which is at least partially non-opaque, having an opacity which is not higher than approximately 70%, and which has a thickness (t) which is less than 50 μm;
   b. arranging said outer enclosure so that it encloses said absorbent units;
   c. arranging said outer enclosure so that it supports a first graphical item; and
   d. arranging at least one of said absorbent units so that it supports a second graphical item, wherein said method comprises:
   e. configuring said absorbent unit which supports said second graphical item so that said second graphical item is positioned so that said second graphical item is not visible for a viewer from outside of the outer enclosure and positioning the absorbent units in a manner so that the second graphical item is covered by the first graphical item.

* * * * *